(12) United States Patent
Luecke et al.

(10) Patent No.: US 7,927,013 B2
(45) Date of Patent: Apr. 19, 2011

(54) COMPUTED TOMOGRAPHY ROTOR, AND GANTRY EMBODYING SAME

(75) Inventors: Daniela Luecke, Germering (DE); Hans-Juergen Mueller, Pretzfeld (DE)

(73) Assignee: Siemens Aktiengesellschaft, Munich (DE)

( * ) Notice: Subject to any disclaimer, the term of this patent is extended or adjusted under 35 U.S.C. 154(b) by 91 days.

(21) Appl. No.: 12/533,184

(22) Filed: Jul. 31, 2009

(65) Prior Publication Data
US 2010/0025591 A1    Feb. 4, 2010

(30) Foreign Application Priority Data
Aug. 1, 2008 (DE) .......................... 10 2008 036 016

(51) Int. Cl.
*H01J 31/50* (2006.01)
*H05G 1/60* (2006.01)
*G01T 1/166* (2006.01)

(52) U.S. Cl. ...................... 378/189; 378/15; 250/363.05

(58) Field of Classification Search ................. 378/1, 4, 378/15, 189, 196, 197; 250/363.05
See application file for complete search history.

(56) References Cited

U.S. PATENT DOCUMENTS

| 7,406,149 B2 * | 7/2008 | Yokoyama et al. ............. 378/15 |
| 7,447,294 B2 * | 11/2008 | Sadotomo et al. ................ 378/4 |
| 2006/0018437 A1 | 1/2006 | Russinger |
| 2007/0064863 A1 | 3/2007 | Buttner et al. |

FOREIGN PATENT DOCUMENTS

| DE | 42 14 858 C1 | 2/1994 |
| DE | 20 2006 004 118 U1 | 8/2007 |

OTHER PUBLICATIONS

U.S. Appl. No. 12/533,228, filed Jul. 31, 2009.
U.S. Appl. No. 12/533,213, filed Jul. 31, 2009.
U.S. Appl. No. 12/533,198, filed Jul. 31, 2009.
U.S. Appl. No. 12/533,148, filed Jul. 31, 2009.

* cited by examiner

*Primary Examiner* — Irakli Kiknadze
(74) *Attorney, Agent, or Firm* — Schiff Hardin LLP

(57) ABSTRACT

A rotor, and a gantry and a computed tomography apparatus with such a rotor, has recess to accommodate at least one component of an image data acquisition device, and the recess is dimensioned such that the component can be inserted therein in a radial direction proceeding away from a rotation center of the rotor and is positively connected with the rotor by an abutment structure provided on the component, as well as by spot connections. This positive fit thus acts in the direction of the centrifugal forces arising upon rotation of the rotor, such that an ejection of the component from the rotor is effectively prevented even given a failure of the spot connections (for example bolt connections) between the rotor 1 and the component.

8 Claims, 1 Drawing Sheet

COMPUTED TOMOGRAPHY ROTOR, AND GANTRY EMBODYING SAME

BACKGROUND OF THE INVENTION

1. Field of the Invention

The invention concerns a rotor, a gantry and a computed tomography apparatus with a rotor on which components of an acquisition device are mounted.

2. Description of the Prior Art

Computed tomography apparatuses enable the reconstruction of three-dimensional slice or volume images of an examination region for diagnostic purposes. The reconstruction of an image ensues on the basis of projections obtained by irradiating a subject with an x-ray fan mean of an examination region from different projection directions, by rotation of an acquisition device, so that measurement data for parallel projections from an angle range of at least 180 degrees plus the fan beam angle are acquired for reconstruction of an image. To achieve the rotation of the acquisition device, the computed tomography apparatus has a gantry having a stationary frame and a rotor mounted so that it can rotate by means of a rotating bearing device components of the acquisition device are mounted on the rotor. The rotor conventionally has a rotor wall in the form of an annular disc and a retention ring running along its outer periphery for mounting the components of the acquisition device.

To avoid movement artifacts in the reconstructed image that can arise due to patient or organ movements, it is sought to select the time window for acquisition of the projections required for reconstruction to be as small as possible by the use of high rotation speeds. Rotation speeds of 210 R/min are achieved in current computer tomography apparatuses. In the future the rotation speeds will likely be increased to at least 300 R/min.

Due to the high rotation speeds, the connections between the components of the acquisition device (in particular between the x-ray radiator and the detector, and the rotor) are severely mechanically stressed. The components are typically attached to the rotor by spot connections, for example by a bolt connection. High stress values are generated in the region around the connection point due to the centrifugal forces that occur upon rotation. Without additional stabilizing measures in this region, there is a risk that, given an increase of the rotor rotation speed, the connections may be broken and the components thrown from the rotor.

SUMMARY OF THE INVENTION

An object of the present invention is to provide a rotor, a gantry and a computed tomography apparatus with a rotor such that the risk of the components being thrown upon rotation of the rotor is reduced in a simple and reliable.

The rotor according to the invention for a gantry of a computed tomography apparatus for mounting of components of an acquisition device is characterized by the rotor having a recess for at least one of the components, the recess being dimensioned such that the components can be inserted therein in a radial direction proceeding away from a rotation center of the rotor and this component is connected with the rotor by an abutment structure and by spot connections such as bolts or screws or welds. The abutment structure is dimensioned larger than the recess, so if the spot connectors fail, the abutment structure precludes the component from being expelled from the recess by centrifugal force.

This manner of attaching the components acts in the direction of the centrifugal forces arising upon rotation, so that it effectively prevents the mounted component (for example the x-ray radiator or the detector) from being thrown from the rotor upon failure of a spot connection (for example a bolt connection). In the simplest case, the abutment structure is in the form of a flange protruding beyond the contour of the component and rigidly formed with the component. This flange rests directly in the edge region of the rotor around the recess. The forces acting on the flange in this case are distributed over an expanded area so that locally only low stress values occur in the region of the spot connections. The risk of an expelled or thrown component is thereby additionally decreased.

In an embodiment of the invention, the rotor has a composite material in the region around the recess, this composite material containing fibers and/or particles as a reinforcement material. The risk of a breaking or tearing of the rotor structure is reduced by a targeted reinforcement of the edge. Moreover, an additional thickening in this region is not needed, thereby achieving a weight savings. A reinforcement also can be produced by integration of prefabricated shaped bodies in the edge region around the recess. The composite material advantageously has a matrix therein, such as a metal matrix or a polymer matrix.

In another embodiment of the invention, the rotor has a rotor wall in the form of a ring rim and a peripheral retention ring provided in the circumferential direction of the ring rim, in which retention ring the recesses are introduced. The retention ring can be arranged peripherally on the outer circumference of the ring rim, but preferably the retention ring is arranged peripherally on the inner circumference of the ring rim. Because the components of the acquisition device (in particular the x-ray radiator and the detector with high rotation masses) and the rotation bearing device are mounted on the same module, namely on the retention ring, in this case a portion of the centrifugal forces that occur upon rotation of the rotor can be introduced into the rotation bearing device of the rotor near the bearing. A deformation of the gantry is largely avoided in this way.

DESCRIPTION OF THE PREFERRED EMBODIMENTS

Figure 1:
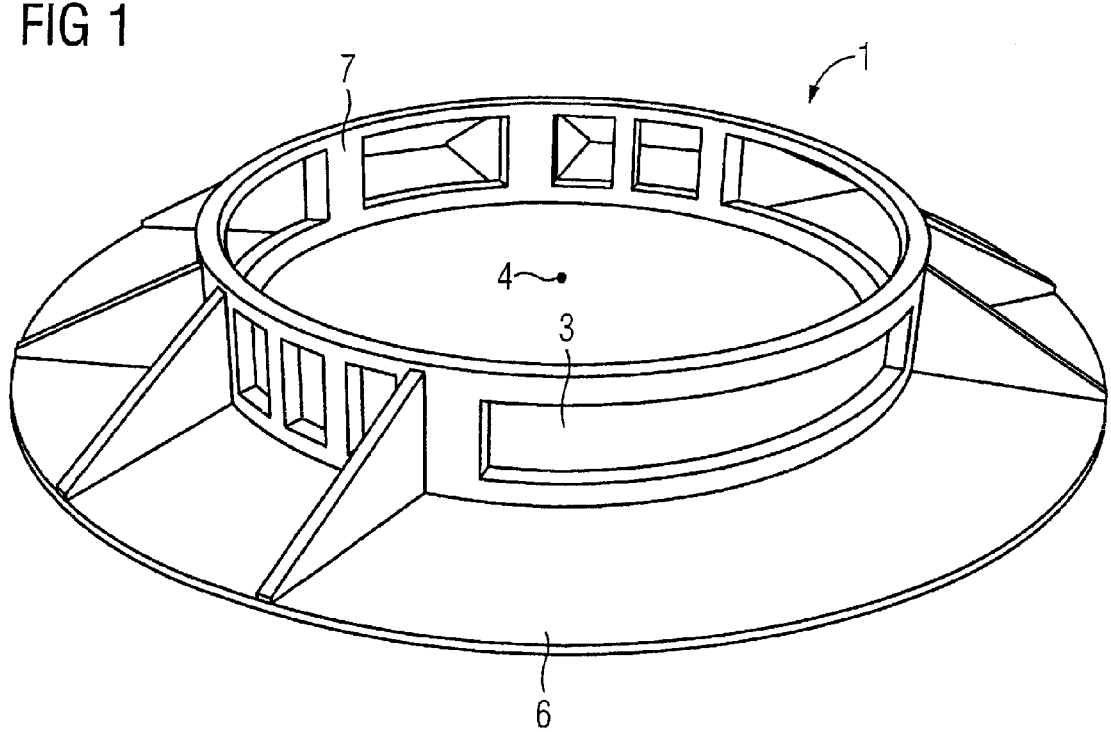
FIG. 1 shows, in perspective view, a rotor according to the invention with a retention ring running around the inner circumference of the ring wheel, the retention ring having recesses for accommodation of components.

A rotor 1 for a gantry of a computed tomography apparatus for mounting components 2 (for example of an acquisition device) is shown in FIG. 1 in a perspective view. The rotor 1 has a rotor wall in the form of a ring rim 6 and a retention ring 7 running around its inner circumference. According to the invention, recesses 3 in which the components 2 can be inserted and mounted are introduced into the retention ring 7. The recesses 3 are dimensioned such that the respective components 2 can be inserted in the radial direction proceeding away from a rotation center 4 of the rotor 1 and can be connected with the rotor 1 by a abutment structure 5 provided at the component 2. Given an inserted component 2, the connection thus acts in the direction of the centrifugal forces arising upon rotation of the rotor 1, such that the expulsion of the component 2 out of the region of the rotor 1 is prevented even given failure of a spot connection (for example a bolt connection) existing between the component 2 and the rotor 1.

The rotor 1 also has a rotation bearing device (not shown in this exemplary embodiment) that interacts with a stationary part of a gantry so that the rotor 1 is supported so that it can rotate. The rotation bearing device is arranged running around the inner circumference of the retention ring 7. The centrifugal forces arising upon rotation are transferred close to the bearing to the stationary part of the gantry via the rotation bearing device. Due to the short force flow, a deformation of the rotor 1 that detrimentally affects the image quality of a generated tomographical image does not occur.

Due to the positive fit between the component 2 and the rotor 1 that acts in the direction of the centrifugal forces, additional measures to prevent the ejection of the component 2 from the region of the rotor 1 can be omitted. In particular a shielding ring running around the outer circumference of the ring wheel 6 (which shielding ring has served in the past to catch components detaching from the rotor 1) is no longer necessary.

Figure 2:
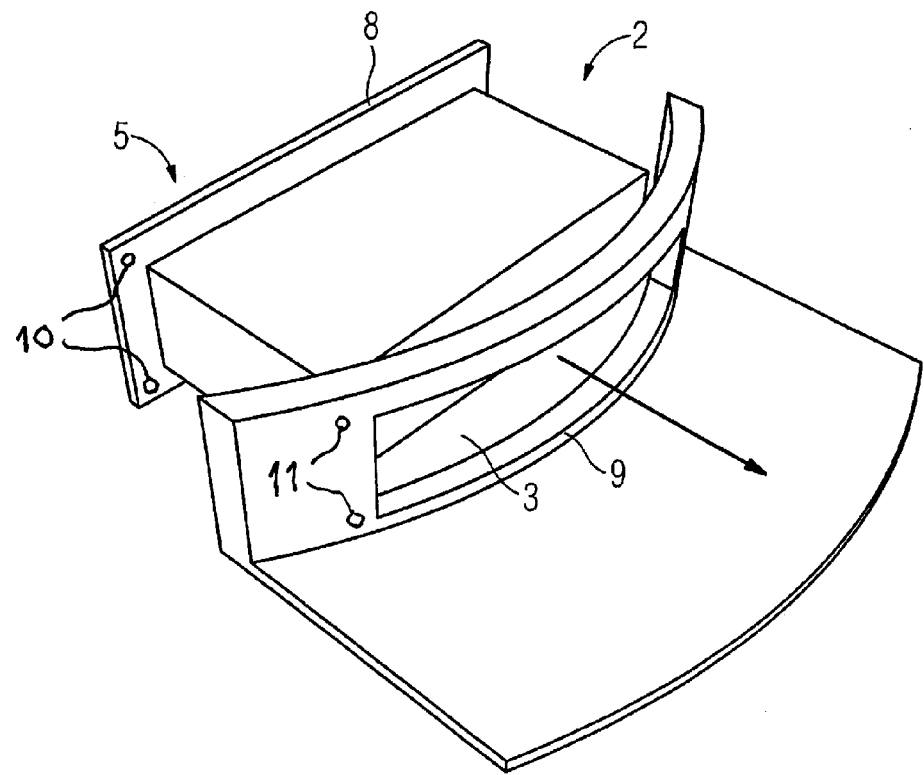
FIG. 2 shows, in an exploded view, a section of the retention ring in the region of a recess and a component to be mounted in the recess.

In the simplest case the component 2 has a flange 8 running around the contour of the component 2 as the abutment structure 5 (shown in FIG. 2). This flange 8 rests directly around the recess 3 in the edge region 9 of the rotor 1 in the inserted state. Due to the larger area of the flange 8, the force acting in the region of the connection point upon rotation of the rotor 1 is reduced per area unit. Only small stress values thus occur in the region of the spot connections, and the danger of an ejection is further decreased.

Reinforcement of the edge region 9 around the recess 3 can be achieved in different ways. For example, a composite material can be used that has fibers and/or particles. This reinforcement material is located in the edge region 9 of the retention ring 7. The danger of a breaking or tearing of the rotor structure is particularly reduced by this targeted reinforcement of the edge region 9, even at high rotation speeds of the rotor 1. The composite material in the edge region 9 can be introduced into the structure of the retention ring 7 by integration of prefabricated shaped bodies, for example. The use of shaped bodies has the advantage that—due to the low expansion of the bodies—the composite materials can be produced under optimal conditions to achieve a specific alignment of the fibers or to achieve a predetermined distribution of the particles. A thickening in the edge region 9 thus can normally be omitted by the use of this type of additional reinforcement, so a weight savings is achieved.

Components 2 that are mounted on the retention ring 7 by the connection (positive fit) described above are, for example, a detector or an x-ray radiator of the acquisition device, or other components that are necessary for operation of the acquisition device or for operation of a cooling device to cool the rotor 1.

In an exploded presentation, FIG. 2 shows a section of the retention ring 7 in the region of a recess 3 and a component 2 to be mounted in the recess 3 in an installation position. As is indicated by the arrow, the component 2 can be inserted into the recess 3 from the radial direction proceeding away from the rotation center of the rotation 1 or in the direction of the centrifugal forces acting upon rotation of the rotor 1. The recess 3 is dimensioned such that, upon insertion of the component 2, the outer contour of the component rests at least in sections essentially on the edge region 9 of the opening formed by the recess.

The component 2 has an abutment structure 5 in the form of a flange 8 projecting beyond the contour, which the flange 8 forms a positive fit with the rotor 1 or with the edge region 9 in the stop position of the component 2. The flange 8 thus lies directly on the structure of the rotor 1 given an established positive fit.

Additional connection means are provided to fix the component in the mounting position. In his exemplary embodiment, the connection means are spot connections in the form of bolt connections. For this purpose the abutment structure 5 of the component 2 has bores 10 (two of which are visible in FIG. 2) that, in the mounting position, are arranged opposite corresponding bores 11 in the structure of the rotor 1. Bolts can be used to affix the component via these bores 10, 11, for example. The bores 10, 11 can be designed such that shaped elements with threads can be used for a simple attachment. To allow a machine processing of the rotor 1 and of the abutment structure 5, inserts made from a metal alloy (for example from an aluminum alloy) can be provided in the region of the bores 10, 11.

The component 2 can be additionally coupled with the rotor wall or the ring rim 6 using further connection means. An improved attachment of the component 2 with the rotor 1 can be achieved in this way. Moreover, an additional connection of the rotor wall can contribute to increasing the rigidity of the rotor structure. In this case the component 2 represents a connection element between the rotor wall and the retention ring with which a portion of the forces arising upon rotation can be passed into the rotation bearing device in an improved manner. The path of the force flow is thus reduced by this connection element, which additionally contributes to an increase of the rigidity. Higher rotor rotation speeds thus can be achieved without significant deformations occurring that lead to a degradation of the image quality in the generated tomographical images.

In summary, the rotor 1, and a gantry and a computed tomography apparatus with such a rotor 1, has recess 3 to accommodate at least one component 2 of an image data acquisition device, and the recess 3 is dimensioned such that the component 2 can be inserted therein in a radial direction proceeding away from a rotation center 4 of the rotor 1 and is positively connected with the rotor 1 by an abutment structure 5 provided on the component 2, as well as by spot connections. This positive fit thus acts in the direction of the centrifugal forces arising upon rotation of the rotor 1, such that an ejection of the component 2 from the rotor 1 is effectively prevented even given a failure of the spot connections (for example bolt connections) between the rotor 1 and the component 2.

Although modifications and changes may be suggested by those skilled in the art, it is the intention of the inventors to embody within the patent warranted hereon all changes and modifications as reasonably and properly come within the scope of their contribution to the art.

We claim as our invention:

1. A rotor for a computed tomography apparatus comprising:
   a rotor structure configured for rotation around a rotation center in a computed tomography apparatus gantry;
   said rotor structure comprising at least one recess configured to receive a component of an image data acquisition system of the computed tomography apparatus by insertion of that component in a radial direction through said recess proceeding away from said rotation center;
   spot connections that connect said component to the rotor structure; and
   an abutment structure connected to the component that is dimensioned to preclude said component from being expelled from said rotor structure through said recess, upon failure of said spot connections, due to centrifugal force acting on said component during rotation of said rotor structure around said rotation center.

2. A rotor as claimed in claim 1 wherein said rotor structure has an edge region proceeding around said recess, and comprising a composite material in said edge region, said composite material comprising a reinforcement material selected from the group consisting of fibers and particles.

3. A rotor as claimed in claim 2 wherein said composite material is integrated into said edge region as a prefabricated shaped body.

4. A rotor as claimed in claim 2 wherein said composite material has a matrix structure, selected from the group consisting of a metal matrix and a polymer matrix.

5. A rotor as claimed in claim 1 wherein said rotor structure comprises a rotor wall formed by a ring rim and a peripheral retention ring proceeding circumferentially around said rotor structure with said ring rim, and wherein said recess is located in said retention ring.

6. A rotor as claimed in claim 5 wherein said retention ring is located peripherally at an outer circumference of said ring rim.

7. A rotor as claimed in claim 5 wherein said retention ring is located peripherally on an inner circumference of said ring rim.

8. A computed tomography gantry comprising:
a stationary frame;
a rotor rotationally mounted in said stationary frame for rotation around a rotation center;
an image data acquisition system comprising a plurality of components mounted on said rotor for co-rotation therewith;
said rotor having a rotor structure with at least one recess therein that receives at least one of said components therein by insertion of said component radially through said recess proceeding away from said rotation center;
spot connections connecting said component to said rotor structure; and
an abutment structure also connecting said component to said rotor structure, said abutment structure being dimensioned to preclude passage of said component through said recess, upon failure of said spot connections, due to centrifugal force acting on said component during rotation of said rotor around said rotation center.

* * * * *